United States Patent [19]

Speidel

[11] 4,036,061
[45] July 19, 1977

[54] BLOOD PRESSURE INDICATOR GAUGE

[76] Inventor: Blasius Speidel, Hochmeisterstrasse 244, 7453 Jungingen, Germany

[21] Appl. No.: 587,641

[22] Filed: June 17, 1975

[51] Int. Cl.² .............................................. A61B 5/02
[52] U.S. Cl. ....................................... 73/410; 73/396; 128/2.05 M
[58] Field of Search ............ 73/396, 410; 116/129 N, 116/129 B, 129 T; 128/2.05 A, 2.05 M, 2.05 G

[56] References Cited

U.S. PATENT DOCUMENTS

| 925,814 | 6/1909 | Jones | 73/396 |
|---|---|---|---|
| 2,630,796 | 3/1953 | Eksten | 73/410 |
| 3,117,570 | 1/1964 | Halasz | 128/2.05 M |

FOREIGN PATENT DOCUMENTS

| 2,209,633 | 9/1973 | Germany |
|---|---|---|
| 392,771 | 10/1965 | Switzerland |

Primary Examiner—S. Clement Swisher
Assistant Examiner—Denis E. Corr
Attorney, Agent, or Firm—Joseph A. Geiger

[57] ABSTRACT

A two-pointer blood pressure indicator gauge with pointer blocking solenoids for the indication of the systolic and diastolic pressures, the gauge having a blocking member or a brake disc directly attached to each of the two pointer shafts, and in which the armature of each solenoid, or a solenoid-actuated brake lever, cooperates with the associated brake member or brake disc, respectively, thereby blocking the spring-driven return motion of the pointers. The pointer for the higher pressure, being dragged by the other pointer during pressure buildup, against a separate spring, is blocked first, allowing the pointer for the lower pressure to continue its return movement until it, too, is blocked.

21 Claims, 3 Drawing Figures

BLOOD PRESSURE INDICATOR GAUGE

BACKGROUND OF THE INVENTION

1. Field of the Invention

The present invention relates to indicator gauges, and more particularly to blood pressure indicator gauges employed in conjunction with blood pressure measuring equipment, where a blood pressure measuring sleeve is applied to a limb and the pressure values and other variables are transmitted to a monitoring console. The special pressure indicator gauge of the invention is adapted for the measurement and recording of two different pressure values by means of two independent pointers which can be blocked at given reading values in response to appropriate signals.

2. Description of the Prior Art

Blood pressure gauges of the above-mentioned type are known in the prior art. They generally feature a rotatable pointer on a pointer shaft to which is attached a return string opposing the movement of the pointer in response to an increase in pressure in a pressure capsule whose expansion drives the pointer shaft via a suitable lever and gear transmission. Such a gauge may further include pointer blocking means consisting of a solenoid and of a blocking member connected to the gear transmission and reaching into the field of the solenoid, for the latter to stop and hold the rotating assembly.

For blood pressure measuring purposes, this type of gauge is normally specially adapted to have two pointers, in order to indicate and record the systolic and diastolic blood pressures of a patient. As the blood pressure measuring sleeve is pressurized, the same pressure also expands the measuring capsule, and this expansion is transmitted to the pointers by means of a suitable translating drive. The latter normally includes a lever converter whose movements are transmitted by a drive arm to a gear segment of large radius which, by engaging a small gear on the pointer shaft, moves the latter in accordance with the pressure acting inside the measuring capsule. The pressure translating drive may further include a drive pin extending laterally from the gear segment and reaching into engagement with a similar second gear segment, engaging a second small gear on the shaft of a second pointer. The shaft of this second pointer is a hollow shaft arranged concentrically with the shaft of the first pointer and located axially between the pointer and gear of the first shaft. In most cases, the hollow shaft is journalled on the shaft of the first pointer. Each pointer is further associated with blocking means consisting of a segment-shaped flat blocking member attached to the large-radius gear segment, and of a blocking solenoid arranged near the periphery of the blocking member, the blocking solenoid being electrically controllable by means of suitable switches. If, following the pressurization of the blood pressure measuring sleeve to a sufficiently high starting value, the pressure in the sleeve and in the measuring capsule is reduced at a controlled rate, both pointers will return under the action of their return springs in accordance with the motions of the translating mechanism, until the blocking solenoid for the second pointer is energized in response to a control signal from the blood pressure measuring device, thereby blocking the second pointer, while the first pointer, continuing its movement, is later similarly blocked by means of its associated blocking solenoid. The blocked positions of the two pointers indicate the systolic pressure and the diastolic pressure, respectively.

Known prior art blood pressure indicator gauges of the aforementioned type have the shortcoming, however, that a certain inaccuracy of reading results from the fact that, although the pointer blocking devices respond quickly, the pointers themselves, which move in response to the geared translating drive in one or the other direction, lag in position behind the actual pressure values by a noticeable amount. This means that the pressure value indicated by a pointer may differ as much as 10 mm Hg from the actual pressure value. Such a deviation from actual pressure values is in many cases unacceptably high.

SUMMARY OF THE INVENTION

It is a primary objective of the present invention to suggest a blood pressure indicator gauge of improved characteristics which gives pressure readings that correspond more accurately to the actual pressure values adjusted in the measuring sleeve of a blood pressure measuring apparatus.

The present invention proposes to attain this objective by suggesting a blood pressure indicator gauge of the above-mentioned type which features a blocking member which is disc-shaped and which is non-rotatably mounted on the shaft of the pointer itself. The direct attachment of the blocking disc to the pointer shaft has the effect that, when the blocking device is actuated, the associated pointer stops immediately at the particular pressure reading. This means that the gear backlash which was present with prior art gear transmissions between the blocking segment and the pointer shaft, and which tended to distort the reading of the latter, is no longer present.

Additional advantageous features of the improved blood pressure indicator gauge are disclosed in the detailed description given below and claimed in the appended claims.

BRIEF DESCRIPTION OF THE DRAWINGS

Further special features and advantages of the invention will become apparent from the description following below, when taken together with the accompanying drawings which illustrate, by way of example, several embodiments of the invention, represented in the various figures as follows.

DESCRIPTION OF THE PREFERRED EMBODIMENTS

Figure 1:
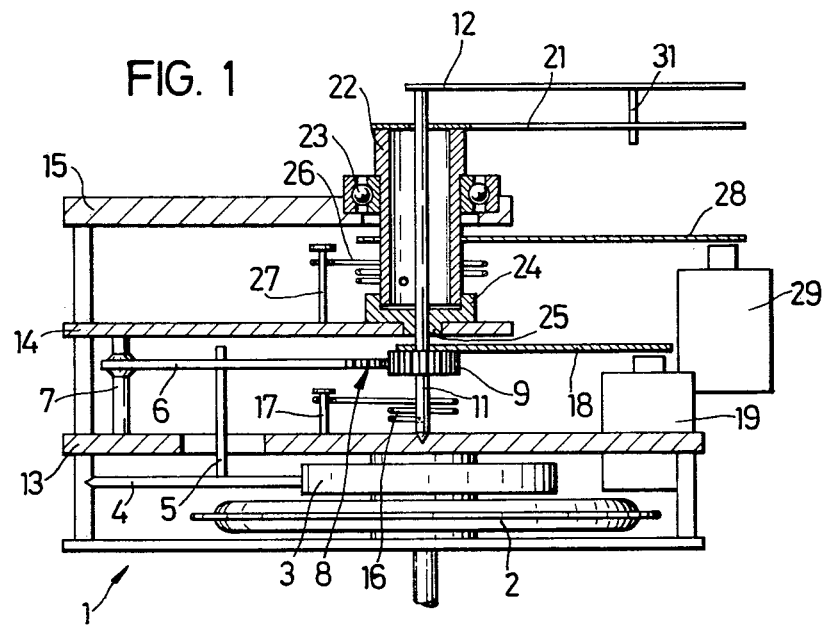
FIG. 1 is a cross section through a blood pressure indicator gauge, representing a first embodiment of the present invention.

Referring to FIG. 1 of the drawing, there is illustrated a blood pressure measuring gauge having an open housing 1 of the plate-and-stud type. Arranged in its lowermost portion is a pressure measuring capsule 2 and a lever converter 3. The converter 3 includes a shaft 4 which extends parallel to the plane of the housing plates, having attached thereto a drive arm 5 extending perpendicularly to the shaft 4 into the upwardly adjacent section of the housing 1. The drive arm 5 executes an angular motion whose median position coincides approximately with a plane through the shaft 4, at right angles to the housing plates. The drive arm 5 engages a gear segment 6 which is pivotably mounted on a pivot shaft 7. The gear segment 6 has a comparatively large radius at which it carries gear teeth 8, meshing with a gear 9 of much smaller diameter. This gear is fixedly mounted on a pointer shaft 11 extending at right angles to the plates of the housing 1, near the center of the latter. One extremity of the pointer shaft 11 is journalled in the intermediate plate 13 of the housing 1, while the midportion of shaft 11 is journalled in the next-higher housing plate 14. The upper extremity of the pointer shaft 11 reaches through the top plate 15 of the housing, carrying a pointer 12 which indicates the diastolic pressure. To the pointer shaft 11 is attached a return spring 16 whose outer end is held by a pin 17 extending from the housing plate 13.

The pointer shaft 11 also carries a blocking member 18, arranged just above the small gear 9 and likewise non-rotatably attached to the shaft 11. The blocking member 18 is a thin flat plate, having the shape of a circular sector or of an annular sector, connected to the pointer shaft 11 by means of a connecting arm. The angular extent of the sector-shaped blocking member corresponds to the angular range covered by the pointer. If necessary, the blocking member may even cover an angle of 360°, meaning that it takes the shape of a circular disc. Facing the peripheral edge portion of the blocking member 18, at a place generally opposite the gear segment 6 in relation to the pointer shaft 11, there is arranged a blocking solenoid 19 whose armature is spaced a small distance from the blocking member 18. The action of the blocking solenoid 19 is controlled by means of electrical controls (not shown), which do not form a part of the present invention.

A second pointer 21, attached to a pointer shaft 22, is arranged above the housing plate 14. The pointer shaft 22 is hollow and concentrically encloses the pointer shaft 11 of the first pointer in an axial area located between the pointer 12 and the upper journal of the first pointer shaft 11 in the housing plate 14. The second pointer shaft 22, in turn, is journalled by means of a radially and axially effective ball bearing 23 mounted inside the housing plate 15 and by means of a radially guiding friction bearing 24 mounted in the housing plate 14. The part which carries the friction bearing 24 has an axial extension 25 engaging a matching bore in the housing plate 14, thereby centering the position of the bearing 24. A central bore inside the extension 25 of the bearing part serves at the same time as the upper journal for the first pointer shaft 11. To the hollow second pointer shaft 22 is likewise connected a return spring 26 whose outer end engages a pin 27 extending upwardly from the housing plate 14. The pointer shaft 22 further carries a blocking member 28 attached to it in the axial space between the two bearings 23 and 24. Like the earlier-described first blocking member 18, the secnd blocking member 28 is a thin flat part, shaped like a circular sector, or like an annular sector connected to the shaft 22 by means of a connecting arm, or, where necessary, extends around the latter in the form of a circular disc. A blocking solenoid 29, similar to the first blocking solenoid 19, is arranged to face the peripheral edge portion of the blocking member 28 in the area generally opposite the gear segment 6 in relation to the pointer shaft axis, the solenoid 29 being likewise controlled by means of electrical controls (not shown) of the blood pressure measuring apparatus.

The second pointer 21 is driven against the bias of the return spring 26 by means of a drive finger 31 connecting it with the first pointer 12. This finger 31 is rigidly attached to the first pointer 12, engaging the second pointer 21 on the side toward which the pointers move, when the pressure in the device falls. The drive finger 31 may also be a flat, lateral extension of the pointer 12, bent over to engage the other pointer in such a way that the two pointers are vertically aligned with one another, as long as they move in unison. This means that the second pointer and its blocking means are designed to indicate the higher of the two pressures, i.e. the systolic pressure, while the first pointer 12 follows the slowly dropping pressure values, as the drive finger 31 moves away from the second pointer 21, until it too, is stopped, giving a reading of the lower diastolic pressure.

Figure 2:
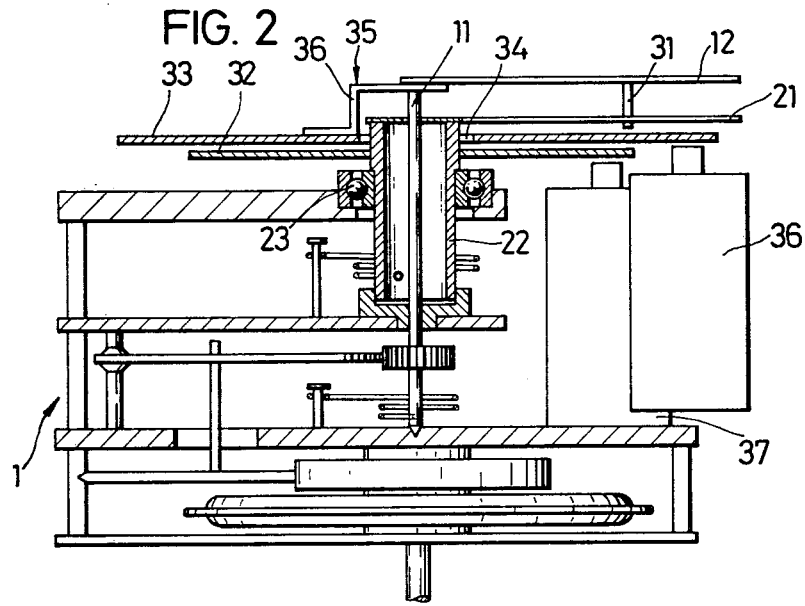
FIG. 2 is similar to FIG. 1, showing a second embodiment of the invention.

In FIG. 2 is illustrated a second embodiment of the invention, showing a modified two-pointer blood pressure measuring gauge for blood pressure measuring devices. While this gauge features essentially the same translating and drive means between the pressure capsule and the pointer shafts 11 and 22, its pointer blocking means are arranged differently in relation to the two pointer shafts. To the extent that reference is being made to parts which have been described earlier in connection with the first embodiment, these parts are to be assumed to have the same reference numerals and to be unchanged from those in FIG. 1.

The modified blocking means of this embodiment features a circular disc 32 attached to the hollow second pointer shaft 22 in an axial shaft portion located above the ball bearing 23, a distance below the second pointer 21. The blocking member for the first pointer 12 is likewise a full circular disc 33 which is attached to the pointer shaft 11. However, since it is necessary to arrange the blocking discs underneath the pointers, the disc 33 is situated axially between the blocking disc 32 and the pointer 21 of the second pointer shaft, without being connected to either of the two. The blocking disc 33, therefore, has an aperture 34 clearing the second pointer shaft 22. The attachment between the blocking disc 33 and the first pointer shaft 11 is obtained by means of a Z-shaped connecting bracket 35 of which one horizontal leg is permanently attached to the disc 33, and the other horizontal leg is non-rotatably connected to the first pointer shaft 11, at a point axially above the second pointer 21. The vertical portion 36 of the Z-shaped connecting bracket thereby spans the upper axial extremity of the hollow second pointer shaft 22 to which the second pointer 21 is attached. Alternatively, the connecting bracket could be U-shaped, with the lower leg of the bracket surrounding the second pointer shaft 22 and having a clearance bore corresponding to the bore 34 of disc 33.

The connecting bracket 35, for purposes of better illustration and description, is shown in FIG. 2 to be located radially opposite the position of the pointers 12 and 21. In actual fact, however, it may be preferable to angularly locate the connecting bracket 35 at such a place that its vertical portion 36 is immediately adjacent to the position occupied by the drive finger 31 on the first pointer 12. This means that the connecting bracket 35 can in fact also fulfill the function of the drive finger 31, which is to establish a dragging drive connection between the two pointers 12 and 21 in the direction of rising pressure, against the bias of the return spring 26 of the second pointer 21. Under these circumstances, the drive finger 31 can be entirely omitted, so that the embodiment of FIG. 2 should be interpreted as not necessitating part 31, if the connecting bracket 35 is assumed to be angularly moved to a position in which its vertical portion 36 takes the place of the drive finger 31.

The arrangement of the two blocking members 32 and 33 above the upper housing plate 15 makes it possible to use full discs as blocking members, which discs may in addition be of comparatively large diameter, unobstructed by the size of the housing 1 and the position of its connecting studs. This feature also makes it possible to use solenoids 37 and 38 of a size which would not fit into the available space of the embodiment of FIG. 1, where, in the case of sector-shaped blocking members, their angular displacements are limited and, in the case of circular discs, their diameter is limited, depending upon the size of the housing 1 and the location of its connecting studs.

Figure 3:
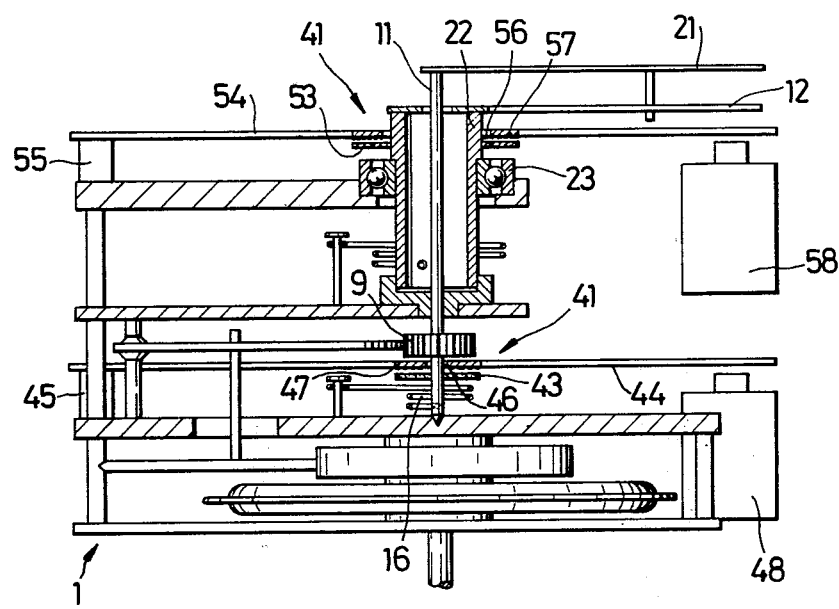
FIG. 3 is also similar to FIG. 1, showing a third embodiment of the invention.

A third embodiment, illustrated in FIG. 3, shows still another arrangement of the blocking means of a two-pointer blood pressure indicator gauge for blood pressure measuring device. To the extent that reference is being made to parts which have been described earlier in connection with the first embodiment, these parts are to be assumed to have the same reference numerals and to be unchanged from those of FIG. 1.

In this embodiment, the blocking members are replaced by two-part assemblies, a blocking assembly 41 for the first pointer 12, and a blocking assembly 42 for the second pointer 21. The first blocking assembly 41 consists of a brake disc 43 of reduced diameter and of a brake lever 44 cooperating with the latter. The brake disc 43 is a small circular disc arranged in the axial space between the gear 9 and the return spring 16, being fixedly mounted on the pointer shaft 11. Above the brake disc 43 is arranged the brake lever 44, spaced a small distance from the brake disc 43, and extending diametrally across the pointer shaft 11. The brake lever 44 is an elongated sheet metal part, one of its extremities being attached to an anchor block 45 located a distance away from the brake disc 43. The lever 44 is comparatively thin in its axial dimension, rendering it flexible in that direction, especially in the length portion immediately adjacent to the anchor block 45. No pivot is therefore necessary, and the attached extremity of the lever 44 may be fixedly connected to the block 45. The flexibility of the brake lever 44 may be localized by reducing the lever portion inwardly adjacent to the anchor block 45 in width and/or thickness. On the other hand, the brake lever 44 may also be stiffened in the area outside its flexing portion, by impressing into its wall suitable longitudinal beads. Thus, the brake lever may be made of thin sheet metal, with the result that it has little weight and a much lower pivoting inertia, as compared to a lever of heavier stock. Such a lever of thin, but appropriately shaped and stiffened sheet metal will therefore not require any weakening in its flexing portion.

In the area of the pointer shaft 11, the brake lever 44 has an appropriate clearance bore 46 for the shaft. Surrounding the bore 46, the brake lever 44 is enlarged to present a brake face 47, corresponding in size to the brake disc 43 arranged just below it. As an alternative to a locally enlarged brake lever 44, it is also possible to attach to the latter a special counter disc with an appropriate center bore, the counter disc being substantially identical in size to the brake disc 43 and attached to the brake lever 44. Diametrally opposite the anchor block 45, the brake lever 44 extends into the field range of the armature of a blocking solenoid 48 which, when energized, pulls the brake lever 44 in the direction against the brake disc 43, thereby engaging the latter.

The blocking effect of the cooperating brake disc 43 and brake face 47 of the brake lever 44 can be increased, by providing special high-friction surfaces on either one or both of the cooperating parts. It is possible, for instance, to apply to the brake lever 44 a circular brake lining which serves as the earlier-mentioned counter disc, while the cooperating face of the brake disc 43 may be appropriately roughened, or vice versa.

The blocking assembly 42 for the second pointer 21 is similar in structure and function to that of the first pointer 11 which has just been described. Its brake disc 53 is arranged above the ball bearing 23 of the hollow pointer shaft 22 and is fixedly attached to the latter. Its cooperating brake lever 54 is again attached to an anchor block 55 on the housing 1. In its center portion, the brake lever 54 has a clearance bore 56 for shaft 22, surrounded by a brake face 57, where the lever 54 is appropriately widened to the diameter of the brake disc 53. The lever portion diametrally opposite the anchor block 55 again reaches into the field of the armature of a blocking solenoid 58 which, when energized, pulls the brake lever 54 downwardly, so that the brake face 57 engages the rotating brake disc 53, stopping and blocking the latter.

The comparatively small diameter of the brake discs 43 and 53 makes it possible to manufacture these discs with much greater planar accuracy than would be possible with the larger sector-shaped or disc-shaped blocking members of the two previously described embodiments. This greater accuracy of the parts makes it possible to correspondingly reduce the clearance between the brake discs and the opposing brake faces of the brake levers, with a corresponding reduction in the necessary pivotal displacement of the brake levers. This means that, when the blocking solenoid is energized, the braking action takes place rapidly and very early, thereby further increasing the accuracy of the gauge reading. A still further advantage of this embodiment resides in the fact that the blocking force exerted by the blocking solenoid against the pointer shaft is in each case axially coincident with the shaft axis, so that a purely axial thrust results, whereaas in the earlier-described embodiments the action of the blocking solenoids causes the blocking discs to exert a canting force on the pointer shaft and on their journals.

It should be understood that the foregoing disclosure describes only preferred embodiments of the invention and that it is intended to cover all changes and modifications of these embodiments of the invention which fall within the scope of the appended claims.

I claim the following:

1. A blood pressure indicator gauge designed for the measurement and the temporary recording of the systolic and/or the diastolic blood pressure of a patient as a component part of a blood pressure measuring apparatus which includes means for generating first and second electrical electrical signals at the instances at which said systolic and diastolic pressures are established, respectively, inside a measuring sleeve of the apparatus, the indicator gauge comprising in combination:

a gauge housing;
   a pointer shaft rotatably journalled in the housing and carrying a pointer attached to one of its extremities;

a return spring connected to the pointer shaft so as to rotationally bias the latter in the direction of a return movement;

a pressure capsule adapted for pressure communication with the measuring sleeve of the apparatus and including mechanical capsule movement translating means which operatively engage the pointer shaft so as to angularly advance the latter in a pushing action in opposition to the rotational return movement bias of the return spring, when the capsule expands in response to a pressure increase; and means for blocking a spring-driven pointer return movement in any pointer position within an angular pressure measurement range, in response to the reception from the apparatus of one of said electrical signals; said pointer blocking means comprising; a first blocking member mounted on the pointer shaft, at a distance from said pointer, for rotation therewith, said blocking member having a generally flat planar surface; a non-rotatable second blocking member supported by the housing so as to be normally positioned a minimal distance from the first blocking member in all positions of the latter within said pressure measurement range; said first and second blocking members being engageable against each other, in response to said one electrical signal, thereby arresting the first blocking member and the shaft and pointer to which member is attached.

2. An indicator gauge as defined in claim 1, wherein the second blocking member is the armature of a solenoid, said armature having a face spaced a small distance from a peripheral edge portion of said first blocking member; and the solenoid is adapted to be energized by said one signal.

3. An indicator gauge as defined in claim 2, wherein the first blocking member is a flat sector-shaped disc.

4. An indicator gauge as defined in claim 2, wherein the first blocking member is a flat circular disc.

5. An indicator gauge mechanism as defined in claim 2, wherein the pointer shaft has two axially spaced journals;

the pointer is attached to the extremity of the pointer shaft at a distance from the closer one of the two journals; and the first blocking member is attached to the pointer shaft axially between the pointer and said closer journal.

6. An indicator gauge as defined in claim 1, further comprising a second pointer shaft rotatably journalled in the housing and carrying a second pointer attached to one of its extremities; the second pointer shaft being hollow and arranged to concentrically surround the first pointer shaft in an axial portion thereof which is located between the extremity at which it carries the first pointer and the point at which it operatively engages the pressure capsule with said translating means;

second pointer blocking means similar to said first-mentioned pointer blocking means and correspondingly associated with the second pointer shaft, the blocking members being engageable against each other in response to the reception from the apparatus of the first one of said electrical signals, thereby arresting the second shaft and pointer, while permitting further return movement of the first pointer; and means associated with the first and second pointers for dragging the second pointer in an angular motion corresponding to that of the first pointer, until said second pointer blocking means becomes operative; and wherein the second pointer is arranged axially a short distance inside the first pointer, meaning that it moves just below the latter.

7. An indicator gauge as defined in claim 6, wherein the hollow second pointer shaft carries, near its extremity to which the second pointer is attached, a ball bearing by which it is journalled in relation to the housing.

8. An indicator gauge as defined in claim 7 wherein the opposite extremity of the hollow second pointer shaft includes a separate bearing by which that shaft extremity is journalled in relation to the housing.

9. An indicator gauge as defined in claim 6, further comprising an independent second return spring operatively connected to the second pointer and biasing the latter in the same sense as the first return spring biases the first pointer; and wherein said second pointer dragging means includes an angular abutment means operatively interposed between the two pointers in such a way that, during an angular advancing motion of the first pointer in response to rising pressure, the abutment means causes the second pointer to execute the same advancing motion, against its return spring, while during an angular return motion of the first pointer in response to falling pressure, the return spring of the second pointer cause the latter to follow such return motion, by holding it in engagement with the first pointer, via said angular abutment means, unless said second pointer blocking means is operative, thereby inhibiting the effect of the second return spring.

10. An indicator gauge as defined in claim 9, wherein the angular abutment means is in the form of a drive finger extending axially from one of the two pointers in the direction of the other pointer, engaging a flask thereof.

11. An indicator gauge as defined in claim 10, wherein said drive finger is an integral part of the first pointer, extending radially inwardly from its trailing flask, in the sense of pointer advance, so as to engage the trailing flank of the second pointer; and the second pointer, when being dragged by the first pointer, is angularly coincident therewith.

12. An indicator gauge as defined in claim 6, wherein the second blocking member of the two pointer blocking means is, in each case, the armature of a solenoid, ech armature having a face spaced a small distance from a peripheral edge portion of its associated first blocking member, and the solenoid of the second pointer blocking means is adapted to be energized by said first electrical signal, indicative of the systolic blood pressure, and the solenoid of the first pointer blocking means is adapted to be energized by said second electrical signal, indicative of the diastolic blood pressure.

13. An indicator gauge as defined in claim 12, wherein the first blocking member of the second pointer blocking means is attached to the hollow second pointer shaft, at an axial distance from the shaft extremity to which the second pointer is attached;

the first blocking member of the first pointer blocking means is located axially between said first blocking member of the second pointer blocking means and said shaft extremity, having an aperture so as not to touch the hollow second pointer shaft; and said first member to the first pointer blocking means includes a connecting bracket attaching it to the first pointer shaft, by reaching axially beyond the extremity of the second pointer shaft.

14. An indicator gauge as defined in claim 13, wherein the connecting bracket includes two radially extending bracket portions by which it is attached to the first blocking member and to the first pointer shaft, respectively, and an intermediate axially extending bracket portion; and the axially extending bracket portion is angularly so positioned that it engages the trailing flank of the second pointer, in the sense of pointer advance, when the two pointers are in substantially the same angular orientation, whereby said connecting bracket serves as the second pointer dragging means.

15. An indicator gauge as defined in claim 1, wherein the first blocking member of the pointer blocking means is a brake disc attached to the pointer shaft so as to rotate therewith;

the second blocking member is an elongated brake lever extending diametrally in relation to the pointer shaft and brake disc and having a brake face adapted to frictionally engage said brake disc;

the brake lever has a fixed and a free end, its fixed end being pivotally anchored to the housing, a distance away from the pointer shaft; and the blocking member engaging means includes spring means normally holding the brake lever spaced a minimal distance from the brake disc, and a solenoid arranged to engage the free end of the brake lever so as to pull the lever into engagement with the brake disc, when the solenoid is energized by an electric circuit.

16. An indicator gauge as defined in claim 15, wherein the brake face of the brake lever has, at least to a large extent, the same circular outline as the brake disc.

17. An indicator gauge as defined in claim 15, wherein the brake lever carries attached thereto a counter-disc whose outer surface constitutes said brake face; and the brake disc and counter-disc have substantially the same diameter.

18. An indicator gauge as defined in claim 15, wherein the brake face and the brake lever and the cooperating face of the brake disc have surfaces which, when axially engaged against each other, produce pointer-shaft-blocking friction at a high friction coefficient.

19. An indicator gauge as defined in claim 18, wherein the brake disc carries a brake lining, and the brake face of the brake lever is roughened.

20. An indicator gauge as defined in claim 15, wherein the fixed end of the brake lever is rigidly anchored to the housing;

the brake lever is resiliently flexible in at least a length portion adjacent to its anchor point with the housing, thereby forming a flexural pivot in relation thereto; and the spring means of the blocking member engaging means is constituted by said flexural pivot.

21. An indicator gauge as defined in claim 20, wherein the brake lever is a stamping of thin sheet metal stock; and at least a major part of that lever portion which is located outside its flexural pivot is stiffened through the impression of stiffening beads into said stamping.

* * * * *